US010143636B2

(12) United States Patent
Watanabe et al.

(10) Patent No.: US 10,143,636 B2
(45) Date of Patent: Dec. 4, 2018

(54) POROUS SILICA PARTICLE AND CLEANSING COSMETIC (71) Applicant: JGC Catalysts and Chemicals Ltd., Kawasaki-Shi, Kanagawa (JP)

(72) Inventors: Satoshi Watanabe, Kitakyushu (JP); Naoyuki Enomoto, Kitakyushu (JP); Yasutaka Miyoshi, Kitakyushu (JP); Michio Komatsu, Kitakyushu (JP)

(73) Assignee: JGC Catalysts and Chemicals Ltd., Kawasaki-Shi, Kanagawa (JP)

( * ) Notice: Subject to any disclaimer, the term of this patent is extended or adjusted under 35 U.S.C. 154(b) by 0 days.

(21) Appl. No.: 15/520,127

(22) PCT Filed: Nov. 5, 2015

(86) PCT No.: PCT/JP2015/081180
§ 371 (c)(1),
(2) Date: Apr. 19, 2017

(87) PCT Pub. No.: WO2016/072456
PCT Pub. Date: May 12, 2016

(65) Prior Publication Data
US 2017/0312196 A1 Nov. 2, 2017

(30) Foreign Application Priority Data
Nov. 5, 2014 (JP) .................. 2014-225107

(51) Int. Cl.
*A61Q 19/10* (2006.01)
*C01B 33/157* (2006.01)
*A61K 8/25* (2006.01)
*A61K 8/02* (2006.01)
*C01B 33/193* (2006.01)

(52) U.S. Cl.
CPC ............. *A61K 8/25* (2013.01); *A61K 8/0279* (2013.01); *A61Q 19/10* (2013.01); *C01B 33/193* (2013.01); *A61K 2800/412* (2013.01); *C01P 2004/03* (2013.01); *C01P 2004/60* (2013.01); *C01P 2004/61* (2013.01); *C01P 2006/12* (2013.01); *C01P 2006/14* (2013.01); *C01P 2006/16* (2013.01); *C01P 2006/17* (2013.01); *C01P 2006/21* (2013.01)

(58) Field of Classification Search
CPC .. A61K 2800/412; A61K 8/0279; A61K 8/25; A61K 6/083; A61K 8/19; A61K 8/29; A61K 6/0008; A61K 6/0088; A61K 6/0235; A61K 6/024; A61K 6/0255; A61K 8/025; A61K 2800/28; A61K 6/0073; A61K 6/0076; A61K 6/0097; A61K 6/0245; A61K 6/027; A61K 2800/60; A61K 2800/805; A61K 8/34; A61K 8/345; A61K 8/365; A61K 8/44; A61K 8/463; A61K 8/602; A61K 8/73; A61K 8/8141; A61K 8/97; C01P 2006/12; C01P 2004/62; C01P 2006/14; C01P 2004/61; C01P 2006/17; C01P 2004/03; C01P 2006/16; C01P 2006/21; C01P 2004/64; C01P 2004/34; C01P 2006/60; C01P 2002/88; C01P 2006/40; C01P 2002/30; C01P 2006/22; C01P 2006/34; C01P 2006/80; C01B 33/18; C01B 33/193; C01B 33/157; C01B 33/12; C01B 33/146; C01B 33/149; C01B 33/126; C01B 33/14; C01B 33/143; C01B 37/00; A61Q 19/10; A61Q 1/02; A61Q 17/04; A61Q 19/00; A61Q 1/12
See application file for complete search history.

(56) References Cited

U.S. PATENT DOCUMENTS

| 2006/0034788 | A1 | 2/2006 | Horino et al. |
| 2008/0107902 | A1* | 5/2008 | Kinuta ............ B01J 4/002 428/402 |
| 2013/0039961 | A1 | 2/2013 | Gonzales et al. |

FOREIGN PATENT DOCUMENTS

| EP | 1493433 A1 | 1/2005 |
| JP | S62275014 A | 11/1987 |
| JP | H10324517 A | 12/1998 |
| JP | 2001278778 A | 10/2001 |
| JP | 2005307120 A | 11/2005 |
| JP | 2011225548 A | 11/2011 |

(Continued)

OTHER PUBLICATIONS

International Search Report dated Dec. 28, 2015 issued in corresponding International Application No. PCT/JP2015/081180.

(Continued)

*Primary Examiner* — Audrea B Coniglio
(74) *Attorney, Agent, or Firm* — Troutman Sanders (57) ABSTRACT A porous silica particle optimized as the scrubbing agent is used for a cleansing cosmetic. The porous silica particle has an average circularity of 0.1 to 0.5, a pore volume of 1.0 to 2.0 ml/g, a mode diameter of 50 to 600 μm, and a ratio of the maximum particle diameter to the mode diameter of 3.0 or less. The porous silica particle moreover has a median size of 0.5 to 25 μm and the maximum particle diameter of 1 to 100 μm, after rubbing with a load of 1.0 to 1.4 KPa for 30 seconds. With the cleansing cosmetic containing this particle, the skin is rubbed by the frictional force generated by the friction with the skin at the rubbing. Therefore, the mild peeling effect for the stratum corneum is obtained and the damage of the skin and the micro damage on the stratum corneum can be prevented.

18 Claims, 2 Drawing Sheets

(56) References Cited

FOREIGN PATENT DOCUMENTS

WO 2012/177757 A2 12/2012

OTHER PUBLICATIONS

Japanese Decision to Grant a Patent dated Apr. 26, 2016 issued in corresponding Japanese Patent Application No. 2016-507721.
Extended European Search Report dated Jul. 26, 2017 for the corresponding European Patent Application No. 15856225.6.

* cited by examiner

FIG. 5

POROUS SILICA PARTICLE AND CLEANSING COSMETIC

CROSS-REFERENCE TO RELATED APPLICATIONS

This is a U.S. national phase application under 35 U.S.C. § 371 of International Patent Application No. PCT/JP2015/081180, filed Nov. 5, 2015, and claims benefit of priority to Japanese Patent Application No. 2014-225107, filed Nov. 5, 2014. The entire contents of these applications are hereby incorporated by reference.

TECHNICAL FIELD

The present invention relates to a porous silica particle and a cleansing cosmetic containing the same, and more particularly to an abrasive porous silica particle.

BACKGROUND

Cleansing cosmetics contain scrubbing agents. The scrubbing agent exfoliates the old stratum corneum by the physical action. As the scrubbing agent, microscopic plastic particles (such as polyethylene particles) have been known (See, for example, Japanese Unexamined Patent Application Publication No. 2001-278778). The plastic particles are lightweight and easily absorb chemical substances such as the pesticide and therefore, it is difficult to remove the plastic particles in the sewage treatment plant. Accordingly, the plastic particles flow into rivers, oceans, ponds, swamps, and the like, and the plastic particles are accumulated in fish and shellfish. Through such fish and shellfish, the plastic particles may have an influence on human bodies.

In recent years, silica-gel particles have also been used as the scrubbing agent. The silica-gel particles can be obtained by the producing methods described in Japanese Unexamined Patent Application Publication Nos. S62-275014 and H10-324517. Japanese Unexamined Patent Application Publication No. 2011-225548 discloses that the scrubbing agent made of particular silica-gel particles provides the user with "the favorable exfoliating property". At the same time, since the silica-gel particles collapse when the particles are rubbed on a subject, the stimulation on the subject is low. This scrubbing agent does not have the above problem of the plastic particles. Further, Patent Literature 4 describes that the crushed silica-gel particles can be used as the silica-gel particles. According to this literature, the spherical silica-gel particles (scrubbing agent) are preferable because such particles feel soft on the skin, and the user of the spherical silica-gel particles feels less tingling feeling after the use.

SUMMARY OF THE INVENTION

The scrubbing agent that leaves less tingling feeling after use tends to be rubbed with the strong pressing force in order to enjoy the desired exfoliating property. From the microscopic point of view, this may cause the micro damage such as the cleansing trace in the stratum corneum and such damage may deteriorate the barrier function and the moisture retaining function of the stratum corneum.

In view of this, it is an object of the present invention to provide a porous silica particle to achieve a cleansing cosmetic that gives less tingling feeling and the sufficient exfoliating property even if rubbed by the weak rubbing force (pressing force).

The porous silica particle according to the present invention has the following characteristics (i) to (vi).

(i) an average circularity of 0.1 to 0.5
(ii) a pore volume (Pv) of 1.0 to 2.0 ml/g
(iii) a mode diameter (Dm) of 50 to 600 μm
(iv) a ratio of a maximum particle diameter (D100) to the mode diameter (Dm), (D100/Dm), of 3.0 or less Moreover, the porous silica particle may have a median size (DR50) of 0.5 to 25 μm and a maximum particle diameter (DR100) of 1 to 100 μm, after rubbing at 1.0 to 1.4 KPa for 30 seconds.

Moreover, the porous silica particle preferably has a ratio of a maximum pore diameter (PD100) to a minimum pore diameter (PD0), (PD100/PD0), of 5 to 10.

Moreover, when a compressive force f1 of 0.5 gf is applied to the porous silica particle, a displacement of 0.5 to 3 μm occurs. Furthermore, when the compressive force that is increased up to 2.5 gf at a proportion of 0.21 gf/sec is applied to the porous silica particle, five or more displacements in a stepwise shape occur, each displacement ranging from 0.01 to 1.0 μm.

By using the aforementioned porous silica particle, the cleansing cosmetic having both the cleansing feeling and the feeling of using the scrubbing agent can be provided.

According to the present invention, the cleansing cosmetic that gives less tingling feeling and the sufficient exfoliating property even if rubbed by the weak rubbing force (pressing force) is provided. Thus, the damage of the skin, and the micro damage on the stratum corneum, such as the linear scar, which may deteriorate the barrier function and the moisture retaining function of the stratum corneum, can be suppressed.

DETAILED DESCRIPTION

A porous silica particle according to the present invention has an average circularity of 0.1 to 0.5, a pore volume of 1.0 to 2.0 ml/g, a mode diameter (Dm) of 50 to 600 μm, and a ratio of the maximum particle diameter (D100) to the mode diameter (Dm), (D100/Dm), of 3.0 or less. Such a porous silica particle is worn down by the frictional force in the rubbing. As a result, the porous silica particle has smaller particle diameter. In addition, after the porous silica particle is rubbed for 30 seconds at 1.0 to 1.4 KPa, this porous silica particle preferably has a median size (DR50) of 0.5 to 25 μm and the maximum particle diameter (DR100) of 1 to 100 μm.

When a micro compressive force is applied to this particle, a micro displacement occurs. Multiple displacements occur repeatedly in the stepwise shape and each displacement is in submicron units. When the cleansing cosmetic containing such porous silica particles as the scrubbing agent is rubbed on the skin, the particles are worn down because of the friction with the skin. This makes the particle diameter smaller. Rubbing the skin with the frictional force leads to the mild peeling effect for the stratum corneum. Along with this, the damage of the skin and the micro damage of the stratum corneum such as the linear scar can be prevented.

The known collapsible silica particles, if collapsed, have the irregularly reduced particle diameters. Thus, it has been difficult to satisfy both the cleansing feeling and the feeling of using the scrubbing agent.

When the compressive force is applied to the porous silica particles according to the present invention, preferably, the displacement as below occurs. When a compressive force of 0.5 gf is applied, a displacement of 0.5 to 3 μm occurs. Alternatively, when a compressive force f2 of 2.5 gf is applied and a displacement of d2 (μm) occurs, the tilt (f2/d2) of the compression displacement is preferably in the range of 0.3 to 2.0. Further alternatively, when the compressive force that is increased up to 2.5 gf at a proportion of 0.21 gf/sec is applied to the porous silica particle, five or more displacements in the stepwise shape occur and each displacement is in the range of 0.01 to 1.0 μm. When the compressive force that is increased at a proportion of 0.21 gf/sec is applied to the porous silica particle, a plurality of displacements in the stepwise shape occurs and a compressive force f3 where the displacement of 10 μm or more occurs first is in the range of 5 to 40 gf. When the amount of compression displacement before the compression displacement of 10 μm or more at the compressive force f3 (gf) occurs is expressed by d3 (μm), the tilt of compression displacement (f3/d3) is in the range of 0.3 to 1.25.

Preferably, the porous silica particles have the following characteristics in predetermined ranges.

(Average Circularity)

The porous silica particles have an average circularity of 0.10 to 0.50, preferably 0.20 to 0.45, and particularly preferably 0.35 to 0.40.

(Pore Volume)

The pore volume is 1.0 to 2.0 ml/g. The particle with a pore volume of 1.0 ml/g or more has the appropriate porosity and not too high particle strength. Therefore, such porous silica particles are easily worn down when rubbed on the skin. Thus, the damage of the skin and the micro damage (such as the linear scar on the stratum corneum) can be suppressed. The particle with a pore volume of 2.0 ml/g or less has not too high porosity and the appropriate wear characteristic. Therefore, the appropriate stimulation (exfoliating property) can be provided at the moment the particles touch the skin. In addition, when a cosmetic is produced using such particles, the cosmetic with the stable quality can be produced because the particles are not worn down easily.

(Maximum Pore Diameter (PD100), Minimum Pore Diameter (PD0))

The maximum pore diameter (PD100) is 15 to 50 nm. The minimum pore diameter (PD0) is 2 to 5 nm. The ratio of the maximum pore diameter (PD100) to the minimum pore diameter (PD0), (PD100/PD0), is in the range of 5 to 10. The particles with the ratio (PD100/PD0) of 5 or more have the appropriate pore diameter distribution and not too high particle strength. Therefore, such particles are easily worn down when rubbed on the skin. As a result, the mild peeling effect is exhibited. Along with this, the damage of the skin and the micro damage on the stratum corneum can be suppressed. The particles with the ratio (PD100/PD0) of 10 or less have not too wide pore diameter distribution and the appropriate particle strength. Therefore, such particles can give the appropriate exfoliating property at the moment when the particles touch the skin.

(Mode Diameter Dm)

The particles have a mode diameter (Dm) of 50 μm or more in order to exfoliate the old stratum corneum by the physical action in rubbing the skin. The particles have a mode diameter of 600 μm or less in order to prevent the damage of the skin and the micro damage on the stratum corneum. The ratio of the maximum particle diameter (D100) to the mode diameter (Dm), (D100/Dm), is 3.0 or less. When this ratio (D100/Dm) is in this range, the damage of the skin and the micro damage on the stratum corneum, which occur in the initial stage of the rubbing after the particles are applied to the skin as the scrubbing agent and before the particles are worn down, can be suppressed. The mode diameter is particularly preferably 2.0 or less.

(Maximum Particle Diameter DR100 and Median Size DR50 after Rubbing)

The porous silica particles rubbed at 1.0 to 1.4 KPa have the maximum particle diameter (DR100) of 1 to 100 μm and a median size (DR50) of 0.5 to 25 μm.

(Specific Surface Area)

The specific surface area obtained by the BET method is preferably 300 to 500 m$^2$/g. When the specific surface area is in this range, both the cleansing feeling and the feeling of using the scrubbing agent can be satisfied. The specific surface area is particularly preferably in the range of 350 to 450 m$^2$/g.

The porous silica particle according to the present invention can be expressed by the median size. The porous silica particles according to the present invention have an average circularity of 0.1 to 0.5, a pore volume of 1 to 2 ml/g, and a median size (D50) of 50 to 500 μm. The porous silica particles have a ratio of the maximum particle diameter (D100) to the median size (D50), (D100/D50), of 3.0 or less. The porous silica particles rubbed with a rubbing load of 250 to 350 g have a median size (DR50) of 0.5 to 25 μm. As the porous silica particles are rubbed, the particles are worn down by the frictional force and have the smaller diameter. The porous silica particles specified by the median size (D50) have the same wear characteristic as the porous silica particles specified by the mode diameter (Dm). The desirable range of each characteristic is also the same. Therefore, the overlapping description is omitted. The following description is made of the matters regarding the median size (D50) that are not described above.

(Median Size D50)

In order to exfoliate the old stratum corneum by the physical action in rubbing the skin, the particles have a median size (D50) of 50 μm or more, preferably 60 μm or more, and more preferably 70 μm or more. In order to prevent the damage of the skin and the micro damage on the stratum corneum by the particles rubbed on the skin, the median size (D50) is 500 μm or less, preferably 480 μm or less, and more preferably 460 μm or less. The ratio of the maximum particle diameter (D100) to the median size (D50), (D100/D50), is 3.0 or less. This ratio may be approximately 2.5. When the ratio (D100/D50) is in this range, the damage of the skin and the micro damage on the stratum corneum, which occur in the initial stage of the rubbing after the particles are applied to the skin as the scrubbing agent and before the particles are worn down, can be suppressed.

(Maximum Particle Diameter DR100 and Median Size DR50 after Rubbing)

The porous silica particles rubbed with a load of 250 to 350 g have the maximum particle diameter (DR100) of preferably 0.7 to 100 µm, and more preferably 1.8 to 80 µm. The median size (DR50) after the rubbing is preferably 0.5 to 25 µm, more preferably 1.0 to 23 µm. The ratio of the maximum particle diameter (DR100) to the median size (DR50) after the rubbing, (DR100/DR50), is preferably 3.0 or less. This ratio may be approximately 1.7. When the cosmetic containing the porous silica particles with such characteristics is rubbed on the skin, the particles will not damage the skin. In addition, the cosmetic with the high scrubbing action that can scrape off the dirt such as sebum in the pores of the skin can be provided.

The porous silica particles may contain, in the range of 0.1 to 10 mass %, a colorant such as iron oxide, titanium dioxide, an ultramarine pigment, a Prussian blue pigment, and an organic pigment in addition to silica as the main component. In consideration of mixing into the cosmetic, the porous silica particle preferably contains amorphous silica.

[Method for Producing Porous Silica Particle]

A method for producing the porous silica particle according to the present invention is shown below.

(Step A)

In this step, slurry of silica-gel is prepared. First, silicate soda (water glass) is added to an acid aqueous solution such as mineral acid, and thus silica particles are generated under the acid condition. Then, alkali such as ammonia is added to make the particles gel. Thus, the slurry of the silica-gel is obtained. In the case of performing desired coloring, the colorant such as iron oxide, titanium dioxide, an ultramarine pigment, a Prussian blue pigment, and an organic pigment is added to the mineral acid or the silicate soda in advance. Alternatively, the colorant may be added to the silicate soda either in the addition or after the addition.

(Step B: Dehydrating Step)

The slurry obtained in Step A is dehydrated using the known solid-liquid separating means, such as filtration or centrifugal separation, so that the silica-gel cake is prepared. In order to remove impurities such as the inorganic salt, the cake is preferably cleaned with pure water.

(Step C: Crushing Step)

The cake obtained in Step B is dried. The drying temperature may be equal to the temperature employed in the case where the silica particle group is obtained by drying the silica-gel. Next, the dried cake is crushed using a crushing means such as a juicer mixer, a roll tumbling mill, a ball mill, or a small-diameter ball mill (bead mill). By the physical crushing, the silica particles have relatively small average circularity (approximately 0.1 to 0.5). Moreover, because of the crushing, the outer shape of the particles easily has the edges. When the rubbing is started, the edges of the particles instantly give the skin the exfoliating property with the hard texture. Therefore, the cleansing with the strong rubbing force (pressing force) can be prevented. Extending the crushing time can reduce the maximum particle diameter (DR100) and the median size (DR50) after the rubbing.

(Step D: Calcination Step)

If the porous silica particles obtained in this manner contain much water, it is preferable to calcine the particles at 250 to 1000° C.

[Cleansing Cosmetic]

The cleansing cosmetic according to the present invention contains the aforementioned porous silica particles and cleansing cosmetic components. The cleansing cosmetic components may be the cosmetic components that are usually used in the cleansing cosmetic compositions. In addition, the cosmetic components described in, for example, Japanese Standards of Quasi-drug Ingredients 2006 (issued by YAKUJI NIPPO LIMITED. on June 16, Heisei 18) and International Cosmetic Ingredient Dictionary and Handbook (issued by the Cosmetic, Toiletry, and Fragrance Association, Fourteenth Edition 2014) can be used.

Such a cleansing cosmetic can be produced by the known method. The high-level mixing technique is not necessarily employed. The cleansing cosmetic is in the form of paste, liquid, gel, or the like. Specific examples include the cleansing cosmetics for body, the cleansing cosmetics for foot, and the cleansing cosmetics for face.

EXAMPLES

Specific examples of the present invention will be described below but the examples will not limit the present invention.

Example 1

(Slurry Preparation Step)

By mixing 20.3 g of a silicate soda (with a silica concentration of 29 wt %) according to JIS3 and 49.1 g of pure water, a silicate soda aqueous solution (with a silica concentration of 8.5 wt %) is obtained. This silicate soda aqueous solution is added by 10.0 g to a sulfuric acid aqueous solution (with a sulfuric acid concentration of 25 wt %) heated to be 40° C., so that slurry A with a pH of 4.0 is prepared. By adding 0.4 g of ammonia water (with an ammonia concentration of 15 wt %) to the slurry A, slurry B is obtained. The slurry B has a pH of 7.0 and a silica concentration of 7.4 wt %. This silica is derived from the silicate soda.

(Dehydrating Step)

The obtained slurry B is filtered through the quantitative filter paper (No. 2, manufactured by Advantec Toyo Kaisha, Ltd.) using the Buchner funnel (3.2 L, made by SEKI-YARIKA Co., Ltd.). After that, the resulting substance is repeatedly cleaned, so that a cake-like substance is obtained.

(Drying/Crushing Step)

The obtained cake-like substance is dried at 120° C. for 12 hours. This dried powder is crushed for 10 seconds using the juicer mixer (manufactured by Hitachi, Ltd.), and thus the powder is obtained.

(Sieving Step)

Figure 1:
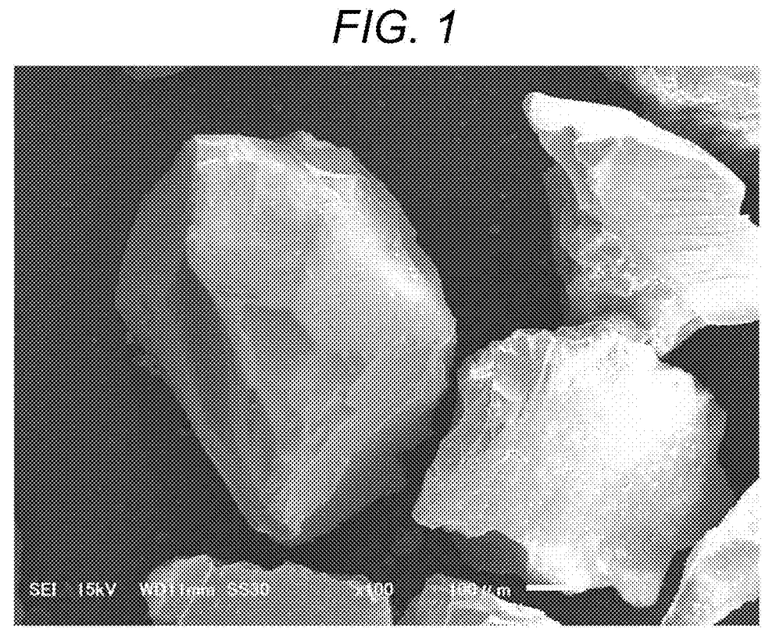
FIG. 1 is a SEM photograph (magnification: 100) obtained by photographing a porous silica particles obtained in Example 1 with a scanning electron microscope.
Figure 2:
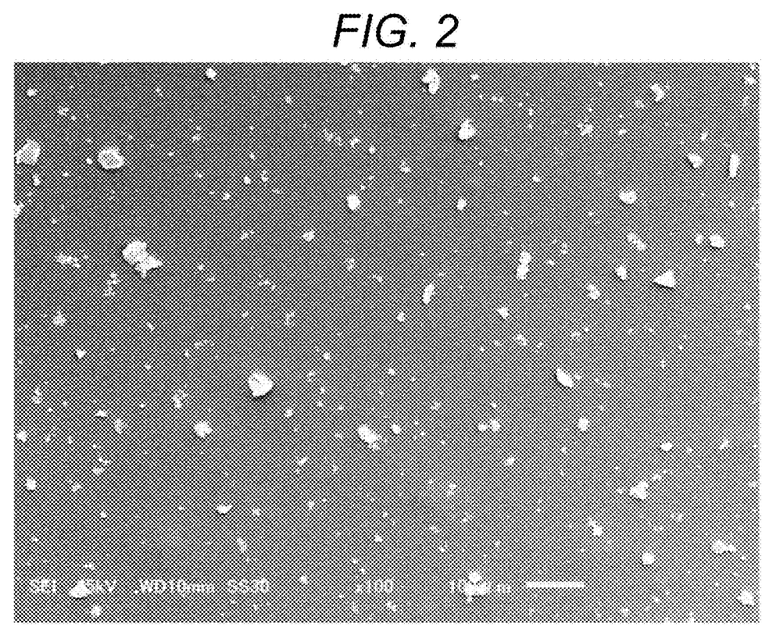
FIG. 2 is a SEM photograph (magnification: 100) obtained by photographing the rubbed porous silica particles in Example 1 with a scanning electron microscope.

Next, this powder is sieved with the 26-mesh sieve (the specification based on JIS test), and thus the powder of the porous silica particles is obtained. The SEM photograph (magnification: 100) obtained by photographing this powder (the porous silica particle group) with a scanning electron microscope is shown in FIG. 1. Moreover, the powder is rubbed for 30 seconds in the arc-like shape with a load of 1.0 to 1.4 KPa, and the SEM photograph (magnification: 100) obtained by photographing the rubbed powder with the scanning electron microscope is shown in FIG. 2. The physical properties of the porous silica particles obtained in the examples are measured and evaluated as below. The results are shown in Table 1.

(1) Average Circularity, Median Size (D50), Mode Diameter (Dm), and Maximum Particle Diameter (D100)

A SEM (scanning electron microscope) photograph (magnification: 100) of the porous silica particle group is taken. The values in title are obtained from the image of 100 to 200 randomly selected particles using the SEM image analysis software (Scandium manufactured by Olympus Corporation).

Specifically, a secondary electron image (SEM photograph) is acquired using the scanning electron microscope JSM-6010LA manufactured by JEOL Ltd. From this SEM photograph, 100 to 200 particles are randomly selected. The image data of the SEM photograph (secondary electron image, 100 times, jpg image) are read by the image analysis software "Scandium". On the image, a particular region is selected as the analysis region (frame). This analysis region (frame) is binarized. Specifically, 153rd gradation as the lower limit value and 255th gradation as the upper limit value are selected for each of RGB values. Based on these two thresholds, the binarization is executed. After the binarization, the particles in the analysis region are detected. Among the detected particles, a group of a plurality of particles detected as one particle is deleted. Various physical property values (the mean diameter and the circularity) of the particle recognized as single particle are obtained. This procedure is repeated until 100 to 200 silica particles are detected and analyzed. Of the physical property values obtained in this manner, the mode diameter, the median size, and the maximum particle diameter are calculated from "the mean diameter" and the average circularity is calculated from the circularities. Note that "the mean diameter (μm)" is the integer obtained by rounding off to the nearest integer. The average circularity is the arithmetic mean value of the circularities of the particles. The circularity of each particle is defined as "circularity=(circumferential length of a circle with the same area as the projected image of the particle)/(circumferential length of the projected image of the particle)".

(2) Specific Surface Area

The powder of the porous silica particles taken by approximately 30 ml in a magnetic crucible (B-2 type) is dried for two hours at 105° C., and then cooled down to the room temperature in a desiccator. Next, the sample is taken by 1 g, and the specific surface area (m$^2$/g) thereof is measured based on the BET method using the full-automatic surface area measuring device (Multisorb 12, manufactured by Yuasa Ionics Inc.). The measured specific surface area is converted with a silica gravity of 2.2 g/cm$^3$, so that the specific surface area per unit mass (m$^2$/cm$^3$) is obtained.

(3) Pore Volume

The powder of the porous silica particles taken by 10 g in a crucible is dried for one hour at 105° C., and then cooled down to the room temperature in a desiccator. Then, 1.0 g of a sample of the powder of the porous silica particles is taken into a well-washed cell. Using a nitrogen adsorption device, nitrogen gas is adsorbed onto the sample. The pore volume thereof is calculated by the following formula:

$$\text{Pore volume (ml/g)}=(0.001567\times(V-Vc)/W)$$

In the above formula, V represents the amount of adsorption (ml) in the standard state at a pressure of 735 mmHg, Vc represents the capacity (ml) of the cell blank at a pressure of 735 mmHg, and W represents the mass (g) of the sample. The density ratio between the nitrogen gas and the liquid nitrogen is 0.001567.

(4) Pore Diameter

The powder of the porous silica particles taken by 10 g in the crucible is dried for one hour at 300° C., input into a desiccator, and then cooled down to the room temperature. Into a glass cell, 0.15 g of the powder of the porous silica particles is taken. Onto the powder of the porous silica particles in the glass cell, nitrogen gas is adsorbed while vacuum deaeration is performed by the Belsorp mini II (manufactured by MicrotracBEL Corp.), and then the nitrogen gas is desorbed. From the obtained adsorption isotherm, the pore diameter distribution is calculated by the BJH method. Thus, the maximum pore diameter (PD100) and the minimum pore diameter (PD0) are obtained.

(5) Maximum Particle Diameter (DR100) and Median Size (DR50) after Rubbing

The artificial skin made of urethane elastomer (bio skin plate, product No. P001-001#20, 195×130×5 Tmm, manufactured by Beaulax) is set on the electronic balance (HF4000, manufactured by A&D Engineering). At a central part of the artificial skin, the slurry formed by adding 3.8 g of pure water to 0.2 g of powder of the porous silica particles is dropped. Subsequently, the slurry is rubbed with four fingers for 30 seconds in the arc-like shape with a load of 250 to 300 g, which implies, assuming the four fingers making a contact area of 4 cm$^2$, the slurry is rubbed under a pressure of 1.0 to 1.4 KPa. The slurry is extracted from the central part of the artificial skin and then photographed with the SEM (scanning electron microscope) (magnification: 100). From the image data of 100 to 200 particles that are randomly selected, the maximum particle diameter (DR100) and the median size (DR50) after rubbing are measured using the aforementioned SEM image analysis software.

(6) Compression Displacement

Figure 3:
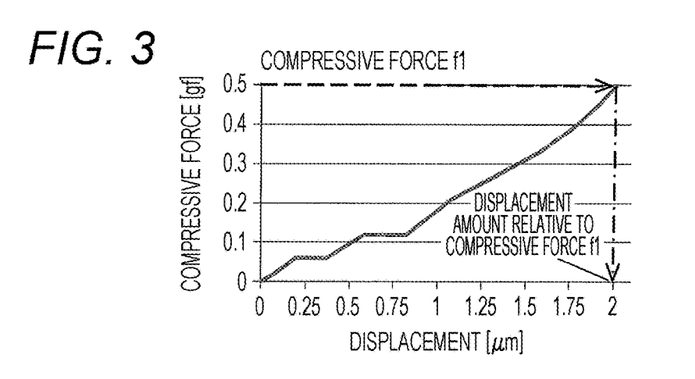
FIG. 3 is a graph expressing the relation between the compressive force and the displacement of the porous silica particle according to Example 1.
Figure 4:
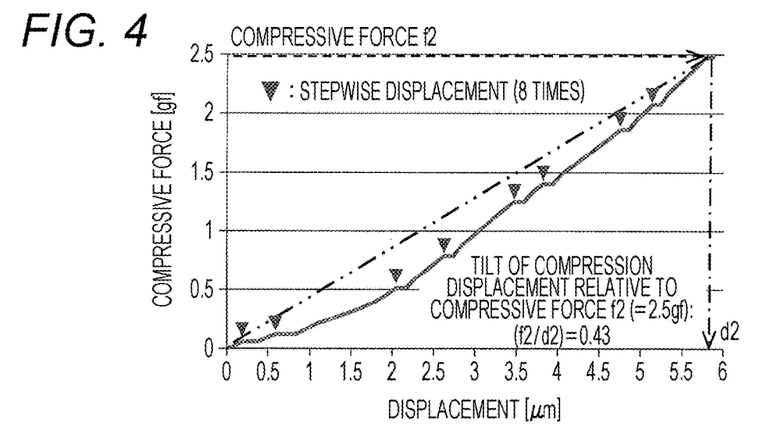
FIG. 4 is a graph expressing the relation between the compressive force and the displacement of the porous silica particle according to Example 1.
Figure 5:
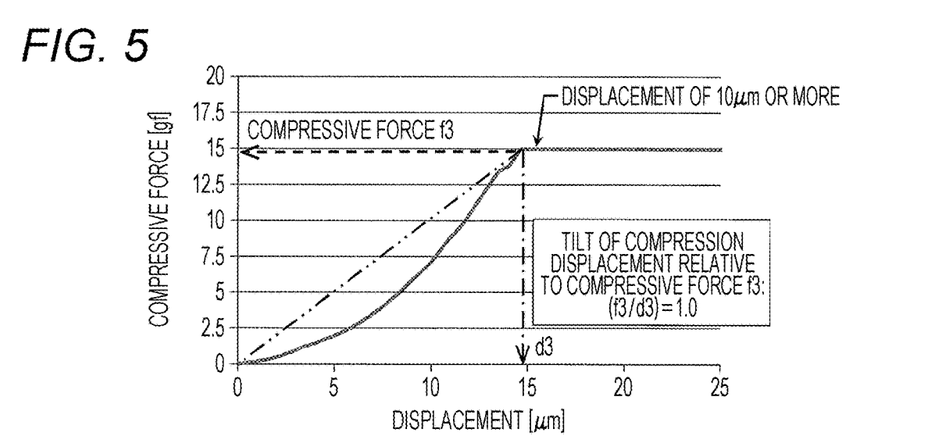
FIG. 5 is a graph expressing the relation between the compressive force and the displacement of the porous silica particle according to Example 1.

The compression displacement that occurs when the compressive force is applied to the porous silica particles is measured using the micro compression tester (MCT-210, manufactured by Shimadzu Corporation). As the indenter, "FLAT 200" (manufactured by Shimadzu Corporation) is used. FIG. 3 to FIG. 5 show the measurement results. FIG. 3 is a graph expressing the displacements of the porous silica particle when a compressive force from 0 to 0.5 gf is applied at a compression speed of 0.21 gf/sec. The amount of displacement at a compressive force of 0.5 gf (compressive force f1) is obtained. In this example, the amount of displacement is approximately 2.0 μm.

FIG. 4 is a graph expressing the displacements of the porous silica particle when a compressive force from 0 to 2.5 gf is applied at a compression speed of 0.21 gf/sec. At this time, a plurality of displacements in the stepwise shape occurs. The stepwise displacements occur at the places on the graph where the displacement increases although the compressive force remains the same. In the graph, each start point of the stepwise displacement is drawn by an inverted triangle. In the present example, eight displacements in the stepwise shape are observed. At this time, each displacement amount is 0.01 to 1.0 μm. The tilt (f2/d2) of the compression displacement is calculated by obtaining the displacement d2 (μm) at a compressive force of 2.5 gf (compressive force f2). In the present example, this tilt is 0.43. The tilt (f2/d2) of the compression displacement is preferably in the range of 0.3 to 2.0.

FIG. 5 is a graph expressing the displacements of the porous silica particle when the compressive force is applied until the stepwise displacement exceeds 10 μm. In this drawing, f3 denotes the compressive force when the stepwise displacement exceeds 10 μm. Here, the compressive force that is increased at a proportion of 0.21 gf/sec is applied. By obtaining the displacement d3 (μm) at the compressive force f3, the tilt (f3/d3) of the compression displacement is calculated. Here, the displacement d3 represents the displacement measured when the stepwise displacement of 10 μm or more starts. In the present example, the tilt of the compression displacement is 1.0. The tilt (f3/d3) of the compression displacement is preferably in the range of 0.3 to 1.25. Note that the application of the compressive force is stopped when the stepwise displacement of 10 μm or more has occurred.

(7) Composition (SiO$_2$ Concentration)

To 0.2 g of the powder of the porous silica particles weighed on a platinum dish, 10 ml of sulfuric acid and 10 ml of hydrofluoric acid are added. The platinum dish is heated on the sand bath until the white smoke of the sulfuric acid comes out. After the cooling, approximately 50 ml of water is added to the residue, and the residue is dissolved into the water with heat. The resulting aqueous solution is cooled, and the aqueous solution is diluted with water; thus, 200 ml of test solution was obtained. The composition of the silica particles in this test solution is obtained using the inductively coupled plasma emission spectroscopy (ICPS-8100 and the analysis software ICPS-8000, manufactured by Shimadzu Corporation).

preparation step. Except this, the same method as that of Example 1 was employed to prepare and evaluate the porous silica particle.

Comparative Example 1

The same method as that of Example 1 is employed to prepare and evaluate the porous silica particle except that the sieving step is not performed. Since the sieving step is not performed, many coarse particles exist, and thus, the maximum particle diameter is large. In this case, even if the rubbing force is weak, the skin may be damaged at the start of the rubbing.

TABLE 1

| | | | Example 1 | Example 2 | Example 3 | Comparative Example 1 | Comparative Example 2 | Comparative Example 3 | Comparative Example 4 | Comparative Example 5 |
|---|---|---|---|---|---|---|---|---|---|---|
| Porous silica particle | Shape | — | Crushing shape | Crushing shape | Crushing shape | Crushing shape | Spherical shape | Crushing shape | Crushing shape | Crushing shape |
| | Median size ($D_{50}$) | μm | 385 | 154 | 391 | 599 | 120 | 25 | 279 | 399 |
| | Mode diameter ($D_m$) | μm | 479 | 190 | 421 | 1239 | 120 | 28 | 312 | 400 |
| | Maximum particle diameter ($D_{100}$) | μm | 628 | 270 | 628 | 4000 | 517 | 49 | 628 | 628 |
| | Average circularity | — | 0.39 | 0.35 | 0.4 | 0.35 | 0.95 | 0.49 | 0.45 | 0.32 |
| | Specific surface area | m$^2$/cm$^3$ | 390 | 395 | 395 | 390 | 250 | 350 | 653 | 50 |
| | Pore volume | ml/g | 1.2 | 1.2 | 1.1 | 1.4 | 0.9 | 1.1 | 2.5 | 0.2 |
| | Maximum pore diameter/minimum pore diameter ($PD_{100}/PD_0$) | — | 9.0 | 7.7 | 6.8 | 8.0 | 7.7 | 6.8 | 10.2 | 4.5 |
| | SiO2 concentration | % | 99.8 | 99.7 | 99.1 | 99.8 | 99.9 | 99.7 | 99.5 | 99.9 |
| | Maximum particle diameter/median size ($D_{100}/D_{50}$) | — | 1.6 | 1.8 | 1.6 | 6.7 | 4.3 | 2.0 | 2.3 | 1.6 |
| | Maximum particle diameter/mode diameter ($D_{100}/D_m$) | — | 1.3 | 1.4 | 1.5 | 3.2 | 4.3 | 1.8 | 2.0 | 1.6 |
| | Median size after rubbing ($D_{R50}$) | μm | 19 | 8 | 8 | 240 | 102 | 21 | 5 | 355 |
| | Maximum particle diameter after rubbing ($D_{R100}$) | μm | 40 | 20 | 20 | 1200 | 414 | 39 | 13 | 628 |
| | Displacement amount relative to compressive force f1 (0.5 gf) | μm | 2.0 | 2.1 | 1.9 | 1.8 | 0.5 | 2.0 | 10 | 0.2 |
| | The number of stepwise displacements by application of compressive force up to 2.5 gf | number of times | 8 | 9 | 11 | 8 | 5 | 10 | 0 | 0 |
| | Compressive force f3 where 10 μm or more displacement occurs | gf | 15.0 | 14.6 | 9.9 | 14.0 | 9.0 | 15.0 | 2.0 | 165.0 |
| | Compression displacement (f2/d2) | | 0.4 | 0.5 | 0.7 | 0.5 | 1.5 | 0.5 | — | 2.5 |
| | Compression displacement (f3/d3) | | 1.0 | 0.9 | 1.1 | 0.9 | 2.0 | 1.0 | 0.1 | 6.6 |

Example 2

The crushing time for the dried powder was changed to 30 seconds. The sieve was changed to the 50-mesh sieve (the specification based on JIS test). Except this, the same method as that of Example 1 was employed to prepare and evaluate the porous silica particle.

Example 3

In this example, 0.06 g of Blue No. 404 is added to 10.0 g of a sulfuric acid aqueous solution (with a sulfuric acid concentration of 25 wt %) heated to be 40° C. in the slurry Comparative Example 2

Spherical porous silica particles are prepared by spraying and drying the slurry B according to Example 1 with the spray drier (OC-25, manufactured by OHKAWARA KAKOHKI CO., LTD.). That is, the slurry B is supplied at a flow rate of 10 L/hr to the rotary atomizer with an entrance temperature of 150° C. and a rotation speed of 2000 rpm, and then the spray drying is performed. In the present comparative example, neither crushing nor sieving is performed. The particles prepared in this manner are spherical.

Therefore, the exfoliating property at the rubbing is weak. As a result, the user rubs the particles for a long time and this may hurt the skin.

Comparative Example 3

The porous silica particles are prepared by the same method as that of Example 1 except that the crushing time is changed to 45 seconds and the sieve is changed to the 281-mesh sieve (the specification based on JIS test). Since the crushing time is long and the sieve has smaller openings, the mean particle diameter is small. Therefore, the exfoliating property cannot be obtained at the rubbing. Thus, the prepared porous silica particles are not suitable for the scrubbing agent.

Comparative Example 4

To the slurry A according to Example 1, 2.1 g of ammonia water was added. From the moment when the pH became 9.0, the stirring was performed for two hours while the temperature was maintained at 40° C. Thus, slurry B with a silicate concentration of 7.3 wt % is prepared. The silicate is derived from the silicate soda. Except this, the same method as that of Example 1 was employed to prepare the porous silica particle. The porous silica particle has large pore volume. Therefore, the exfoliating property by the rubbing is not obtained. Since the pore volume is large, the large displacement occurs even with the small compressive force. As shown in Table 1, the stepwise displacement of 10 μm or more occurs at a compressive force of 2.0 gf.

Comparative Example 5

The dried powder according to Example 1 is calcined for 6 hours at 1000° C. This calcined powder is crushed for 10 seconds using the juicer mixer (manufactured by Hitachi, Ltd.) and thus the powder is obtained. Next, this powder is sieved with the 26-mesh sieve (the specification based on JIS test), and thus, the powder of the porous silica particles is obtained. In the present comparative example, the calcination is performed at high temperature. Therefore, the pore volume is small and the wear by the rubbing is less likely to occur. Accordingly, the skin may be damaged by the rubbing.

[Preparation and Evaluation of Cleansing Cosmetic]

The powder of the porous silica particles prepared in the above examples and comparative examples, which corresponds to a component (1), and other components (2) to (15) were put into a beaker to satisfy the mixing ratio (mass %) shown in Table 2. These components are stirred with a homogenizer. Thus, the uniformly mixed cleansing cosmetic for body is obtained.

TABLE 2

| Cosmetic components of cleansing cosmetic for body | Mixing amount (mass %) |
|---|---|
| (1) Porous silica particles according to Example or Comparative Example | 5.00 |
| (2) Water | 44.64 |
| (3) Sodium Lauryl Sulfate | 24.00 |
| (4) Acrylates/C10-30 Alkyl Acrylate Crosspolymer | 10.00 |
| (5) Corn Powder Hydrolysate | 8.00 |
| (6) Propanediol | 5.20 |
| (7) Carrageenan | 0.80 |
| (8) Sodium Chloride | 0.50 |
| (9) Phenoxyethanol, Ethylhexylglycerin | 0.50 |

TABLE 2-continued

| Cosmetic components of cleansing cosmetic for body | Mixing amount (mass %) |
|---|---|
| (10) Flavoring Agent | 0.50 |
| (11) Xanthan Gum | 0.40 |
| (12) Sodium Laurylglucosides Hydroxypropylsulfonate | 0.30 |
| (13) Sodium Hydroxide | 0.10 |
| (14) Lactic Acid | 0.05 |
| (15) EDTA-2Na | 0.01 |

Thus, the cleansing cosmetics for body A to C in which the porous silica particles according to the examples are mixed, and the cleansing cosmetics for body a to e in which the porous silica particles according to the comparative examples are mixed are obtained.

In regard to these cleansing cosmetics, twenty panelists conducted the sensory test. The following five items were examined by hearing from the twenty panelists: the exfoliating property, no tingling feeling, the luster of the cleansed skin, no dulness of the cleansed skin, and no tingling feeling of the cleansed skin. The results were evaluated based on the following criteria A. Moreover, the points given by the panelists were totaled and how the panelists felt when using the cleansing cosmetics was evaluated based on the following evaluation criteria B.

Evaluation Criteria A
  5: Excellent
  4: Good
  3: Average
  2: Poor
  1: Very poor Evaluation Criteria B
  Double circular mark: 80 or more points in total
  Single circular mark: 60 or more and less than 80 points in total
  White triangular mark: 40 or more and less than 60 points in total
  Black triangular mark: 20 or more and less than 40 points in total
  Cross mark: less than 20 points in total The evaluation results are shown in Table 3. The user felt very well with the cosmetics A to C either in the cleansing or after the cleansing. On the other hand, the user did not feel well with the cosmetics a to e.

TABLE 3

| | | During cleansing | | After cleansing | | |
|---|---|---|---|---|---|---|
| Evaluation sample | | Exfoliating property | No tingling feeling | Luster of skin | No dulness of skin | No tingling feeling |
| Example | Cosmetic A | ◎ | ○ | ◎ | ○ | ○ |
| | Cosmetic B | ○ | ○ | ◎ | ◎ | ◎ |
| | Cosmetic C | ◎ | ◎ | ◎ | ○ | ○ |
| Comparative Example | Cosmetic a | ◎ | X | X | ○ | X |
| | Cosmetic b | ○ | X | ○ | ○ | X |
| | Cosmetic c | X | ◎ | X | X | ◎ |
| | Cosmetic d | X | ○ | X | X | ○ |
| | Cosmetic e | ◎ | X | X | △ | X |

The invention claimed is:

1. Porous silica particles comprising:
an average circularity of 0.1 to 0.5, the average circularity obtained from image data of 100 to 200 particles selected randomly from an SEM-photograph of a porous silica particle group;

a pore volume of 1.0 to 2.0 ml/g, the pore volume (Pv) obtained by a nitrogen adsorption method;

a mode diameter of 50 to 600 μm, the mode diameter ($D_m$) obtained from the image data of 100 to 200 particles selected randomly from the SEM-photograph of the porous silica particle group; and a ratio ($D_{100}/D_m$) of a maximum particle diameter ($D_{100}$) to the mode diameter ($D_m$) of 3.0 or less, the maximum particle diameter ($D_{100}$) is obtained from the image data of 100 to 200 particles selected randomly from the SEM-photograph of the porous silica particle group.

2. The porous silica particles according to claim 1, further comprising a median diameter after rubbing ($D_{R50}$) of 0.5 to 25 μm and a maximum particle diameter after rubbing ($D_{R100}$) of 1 to 100 μm, the median diameter after rubbing ($D_{R50}$) and the maximum particle diameter after rubbing ($D_{R100}$) are obtained from the image data of 100 to 200 particles selected randomly from the SEM-photograph of the porous silica particle group after rubbing at 1.0 to 1.4 KPa for 30 seconds.

3. The porous silica particles according to claim 1, further comprising: a maximum pore diameter ($PD_{100}$) of 15 to 50 nm, the maximum pore diameter obtained from a pore diameter distribution calculated from an adsorption isotherm by the BJH method;

a minimum pore diameter ($PD_0$) of 2 to 5 nm, the minimum pore diameter is obtained from the pore diameter distribution calculated from the adsorption isotherm by the BJH method; and a ratio ($PD_{100}/PD_0$) of the maximum pore diameter to the minimum pore diameter is 5 to 10.

4. The porous silica particles according to claim 1, wherein when a compressive force of 0.5 gf is applied to the porous silica particle, a displacement of 0.5 to 3 μm occurs.

5. The porous silica particles according to claim 4, wherein when the compressive force that is increased up to 2.5 gf at a proportion of 0.21 gf/sec is applied to the porous silica particle, five or more displacements occur in a stepwise shape, each displacement ranging from 0.01 to 1.0 μm.

6. The porous silica particles according to claim 1, wherein when an amount of displacement at a compressive force of 2.5 gf applied to the porous silica particle is expressed by the displacement (μm), a tilt of compression displacement is in the range of 0.3 to 2.0.

7. The porous silica particles according to claim 1, wherein when the compressive force that is increased at a proportion of 0.21 gf/sec is applied to the porous silica particle, a plurality of displacements in a stepwise shape occurs and a compressive force at which the displacement of 10 μm or more occurs first is in the range of 5 to 40 gf.

8. The porous silica particles according to claim 7, wherein when an amount of compression displacement before the compression displacement of 10 μm or more at the compressive force (gf) occurs is expressed by the displacement (μm), a tilt of compression displacement is in the range of 0.3 to 1.25.

9. Porous silica particles comprising:
an average circularity of 0.1 to 0.5, the average circularity is obtained from image data of 100 to 200 particles selected randomly from an SEM-photograph of the porous particle group;

a pore volume of 1 to 2 ml/g, the pore volume (Pv) is obtained by the nitrogen adsorption method;

a median diameter of 50 to 500 μm, the median diameter ($D_{50}$) is obtained from the image data of 100 to 200 particles selected randomly from the SEM-photograph of the porous silica particle group;

a ratio ($D_{100}/D_{50}$) of a maximum particle diameter ($D_{100}$) to the median diameter (D50) of 3.0 or less, the maximum particle diameter ($D_{100}$) is obtained from the image data of 100 to 200 particles selected randomly from the SEM-photograph of the porous silica particle group; and a median diameter after rubbing of 0.5 to 25 μm, the median diameter after rubbing ($D_{R50}$) is obtained from the image data of 100 to 200 particles selected randomly from the SEM-photograph of the porous silica particle group after rubbing with a load of 250 to 350 g.

10. A cleansing cosmetic comprising:
the porous silica particles according to claim 1, and
a cleansing cosmetic component.

11. The porous silica particles according to claim 2, comprising a ratio of a maximum pore diameter to a minimum pore diameter of 5 to 10.

12. The porous silica particles according to claim 2, wherein when a compressive force of 0.5 gf is applied to the porous silica particle, a displacement of 0.5 to 3 μm occurs.

13. The porous silica particles according to claim 2, wherein when the compressive force that is increased up to 2.5 gf at a proportion of 0.21 gf/sec is applied to the porous silica particle, five or more displacements in a stepwise shape occur, each displacement ranging from 0.01 to 1.0 μm.

14. The porous silica particles according to claim 2, wherein when an amount of displacement at a compressive force of 2.5 gf applied to the porous silica particle is expressed by the displacement (μm), a tilt of compression displacement is in the range of 0.3 to 2.0.

15. The porous silica particles according to claim 2, wherein when the compressive force that is increased at a proportion of 0.21 gf/sec is applied to the porous silica particle, a plurality of displacements in a stepwise shape occurs and a compressive force at which the displacement of 10 μm or more occurs first is in the range of 5 to 40 gf.

16. The porous silica particles according to claim 15, wherein when an amount of compression displacement before the compression displacement of 10 μm or more at the compressive force (gf) occurs is expressed by the displacement (μm), a tilt of compression displacement is in the range of 0.3 to 1.25.

17. A cleansing cosmetic comprising:
the porous silica particles according to claim 2, and
a cleansing cosmetic component.

18. A cleansing cosmetic comprising:
the porous silica particles according to claim 9, and
a cleansing cosmetic component.

* * * * *